United States Patent [19]
Coyle et al.

[11] Patent Number: 6,156,946
[45] Date of Patent: Dec. 5, 2000

[54] BIOLOGICAL ACTIVATION OF AROMATICS FOR CHEMICAL PROCESSING AND/OR UPGRADING OF AROMATIC COMPOUNDS, PETROLEUM, COAL, RESID, BITUMEN AND OTHER PETROCHEMICAL STREAMS

[75] Inventors: Catherine L. Coyle, Mendham; Michael Siskin, Randolph; David T. Ferrughelli, Flemington; Michael S. P. Logan, Phillipsburg; Gerben Zylstra, Roosevelt, all of N.J.

[73] Assignee: Exxon Research and Engineering Company, Florham Park, N.J.

[21] Appl. No.: 09/415,085

[22] Filed: Oct. 8, 1999

Related U.S. Application Data

[63] Continuation of application No. 09/110,086, Jul. 2, 1998, abandoned, which is a continuation of application No. 08/631,864, Apr. 12, 1996, abandoned.

[51] Int. Cl.[7] .............................. C10G 32/00; C07C 5/00; C12P 7/22
[52] U.S. Cl. .................... 585/264; 585/266; 208/414; 208/433; 208/435; 435/58; 435/156
[58] Field of Search .................................. 585/261, 264, 585/268, 272, 266; 208/56, 211, 214, 219, 228, 254 H, 403, 414, 433, 435; 435/117, 119, 120, 58, 29, 155, 156, 280, 60; 568/771

[56] References Cited

U.S. PATENT DOCUMENTS

| | | | |
|---|---|---|---|
| 4,152,361 | 5/1979 | Imai | 585/353 |
| 4,153,509 | 5/1979 | Schwartz | 195/51 R |
| 4,508,918 | 4/1985 | Yasuhara et al. | 560/241 |
| 4,555,373 | 11/1985 | Higgins | 435/132 |
| 4,833,269 | 5/1989 | Schroeder | 562/484 |
| 5,002,888 | 3/1991 | Killbane, II | 435/252.31 |
| 5,105,025 | 4/1992 | Spivack et al. | 568/720 |
| 5,169,550 | 12/1992 | Sanderson et al. | 252/52 R |
| 5,217,884 | 6/1993 | Zimmermann et al. | 435/117 |
| 5,262,373 | 11/1993 | Durand et al. | 502/255 |
| 5,306,625 | 4/1994 | Kiener et al. | 435/41 |
| 5,607,857 | 3/1997 | Grossman et al. | 435/282 |
| 5,616,496 | 4/1997 | Frost et al. | 435/252.3 |

OTHER PUBLICATIONS

The Soluble Methane Mono–oxygenase of Methylococcus capsulatus (Bath); Its Ability to Oxygenate n–Alkanes, n–Alkenes, Ethers, and Alicyclic, Aromatic and Heterocyclic Compounds, by John Colby, David I. Stirling and Howard Dalton; Biochem. J. (1977) 165, 395–402.

*Primary Examiner*—Bekir L. Yildirim
*Attorney, Agent, or Firm*—Ronald D. Hantman

[57] ABSTRACT

The present invention is a process for transforming aromatic organic compounds and resource materials. The process includes the steps of contacting an organic material selected from the group consisting of single and/or multi-ring aromatic compounds and alkylaromatic compounds, and their heteroatom-containing analogues, crude oil, petroleum, petrochemical streams, coals, shales, coal liquids, shale oils, heavy oils and bitumens with a microorganism or enzymes in order to hydroxylate the organic material, followed by contacting the hydroxylated organic resource material so as to cause hydrogenation and/or hydrogenolysis on the material.

21 Claims, No Drawings

BIOLOGICAL ACTIVATION OF AROMATICS FOR CHEMICAL PROCESSING AND/OR UPGRADING OF AROMATIC COMPOUNDS, PETROLEUM, COAL, RESID, BITUMEN AND OTHER PETROCHEMICAL STREAMS

This application is a continuation of Ser. No. 09/110,086 filed Jul. 2, 1998 now abandoned, which is a continuation of Ser. No. 08/631,864 filed Apr. 12, 1996, now abandoned.

BACKGROUND OF THE INVENTION

This invention relates to the transformation of organic compounds. In particular, the invention is a process to transform organic material by biological hydroxylation followed by hydrogenation and/or hydrogenolysis.

Transformations of organic compounds in aqueous environments are of considerable intrinsic interest and of great economic importance. Most of the world's fuel sources and synthetic fuel precursors have been naturally formed and modified under such conditions. The potential economic incentives for converting and upgrading organic-containing resource materials by aqueous rather than conventional hydrogen treatments is enormous. Despite the scientific and economic importance, available work on reactions of organic compounds and resource materials in water at temperatures above about 100° C. has been sparse and fragmentary.

Important reactions in the processing of petrochemical and other heavy hydrocarbon streams containing aromatic compounds involve the activation of aromatic rings by hydrogenation and subsequent reactions that result in cracked and ring-opened products. In this invention, a process is provided that combines the use of a biological organism or catalyst to produce hydroxylated products, thereby activating the feed for further chemical hydrogenation, cleavage and upgrading. The subsequent chemical processing might include conventional hydrotreating, aqueous/CO treatment or other chemical processing and upgrading chemistry.

SUMMARY OF THE INVENTION

The present invention is a process for transforming aromatic organic compounds and resource materials. The process includes the steps of contacting an organic material selected from the group consisting of single and/or multi-ring aromatic compounds and alkylaromatic compounds, and their heteroatom-containing analogues, crude oil, petroleum, petrochemical streams, coals, shales coal liquids, shale oils, heavy oils and bitumens with a microorganism or enzymes in order to hydroxylate the organic material, followed by contacting the hydroxylated organic resource material so as to cause hydrogenation and/or hydrogenolysis on the material.

DESCRIPTION OF THE PREFERRED EMBODIMENT

The present invention is a process to transform an aromatic organic material into more useful products. The first step in the process is the hydroxylation of the material using microorganisms or other biocatalysts. The hydroxylated material is then transformed by hydrogenation and/or hydrogenolysis.

Hydroxylation of the aromatic rings in a variety of hydrocarbon and heteroatom-containing aromatic compounds activates them for hydrogenation and cleavage under e.g., aqueous/CO conditions. For example, biphenyl is unreactive under aqueous/CO conditions even at temperatures exceeding 400° C. Hydroxylation of the biphenyl ring however activates the biphenyl for subsequent hydrogenation and cleavage. Similar results were obtained using aqueous/CO chemistry on a variety of multi-ring aromatic compounds. Aqueous/CO treatment also results in removal of S and N from hydroxylated heteroatom-containing aromatic compounds. In addition, U.S. Pat. No. 5,910,440 discloses the oxidation of the heteroatoms in compounds such as dibenzothiophene results in activation and heteroatom removal by subsequent aqueous/CO processing. This invention provides a way to use a biological process to oxidize or hydroxylate the feed thereby activating it for subsequent chemical processing.

A. Hydroxylation

Microorganisms often aerobically degrade aromatic compounds through the introduction of molecular oxygen into the aromatic nucleus. One class of enzymatic reaction of this type involves a monooxygenase in which case the product is a singly hydroxylated aromatic compound. Alternatively, and more commonly for neutral aromatic compounds, the initial enzymatic step involves a dioxygenase enzyme. The product of this reaction is a cis-dihydroxy non-aromatic compound. A subsequent enzymatic step catalyzed by a dehydrogenase enzyme converts the cis-dihydrodiol into a 1,2-dihydroxyaromatic compound. Alternatively, the cis-dihydrodiol can be chemically dehydrated to a monohydroxyaromatic compound through dehydration (using acid, base, heat, etc.). The ratio of the hydroxylated compounds produced is dependent on dehydration conditions. Thus, a mutant strain or a set of cloned genes can be used to convert an aromatic compound into either the cis-dihydrodiol (to ultimately produce the monohydroxyaromatic compound) or the 1,2-dihydroxyaromatic compound.

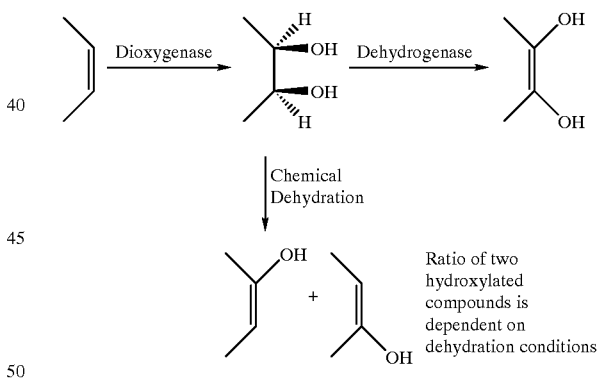

Many different bacterial strains can be isolated that degrade a particular aromatic compound through a dioxygenase type of catabolic pathway. Each aromatic degradative pathway has a particular range of compounds that can be utilized in either catabolic or cometabolic reactions. First, a particular strain could be mutated to change the gene for a particular enzyme so that the enzymatic reaction does not take place. A mutation in the gene for the dehydrogenase would thus cause the cis-dihydrodiol to accumulate while a mutation in the catechol dioxygenase gene would cause the 1,2-dihydroxylated aromatic compound to accumulate. A second method involves the use of the cloned genes expressed in a particular host strain. For instance, E. coli expressing the cloned genes for a dioxygenase will be able to catalyze the formation of a cis-dihydrodiol from a particular starting aromatic compound. E. coli expressing the cloned genes for both the dioxygenase and the dehydrogenase will catalyze the formation of a 1,2-dihydroxylated aromatic compound.

A mutant strain has an advantage over a strain containing the cloned genes. However, the mutation must be stable and the organism must not revert to the wild type. High expression of the genes and significant and rapid cell growth are often easier to obtain in cloned organisms. Often the cloned genes in a given host strain can be more easily controlled. The desired enzymatic activity can be produced on demand using inducing agents. The level of enzyme activity is often higher than that obtained with mutant strains and thus the biotransformation rate can be much higher. The host organism can be selected for particular traits desired for enhanced biotransformation. One example of this is the use of a solvent resistant strain as a host in order to increase the accessibility of the target aromatic in a two phase organic-aqueous system. Such microorganisms can be active in non-aqueous media as long as traces of water are present; enough to form a few mono-layers at the active site. Finally, desired activity can be obtained by using partially purified or purified enzymes from the appropriate strains. Due to the aqueous nature of the subsequent hydrogenation and hydrogenlysis steps, separation of water from the fuel is not necessary. Substrates for these strains include monocyclic compounds such as benzene or toluene; bicyclic compounds such as naphthalene and biphenyl, polycyclic compounds such as phenanthrene, anthracene, pyrene and chrysene and their substituted and heteroatom containing derivatives as well as real feeds.

B. Hydrogenation and Hydrogenolysis

1. Aqueous Treatment

The process of the present invention is typically carried out at temperatures from about 200° C. to about 600° C. More preferably temperatures from about 250° C. to about 550° C. and most preferably temperatures from about 300° C. to about 500° C. may be used. When a base is not employed in combination with carbon monoxide, the carbon monoxide should be introduced into the aqueous system taking more care to form and maintain a sufficient concentration of species capable of transferring hydride ions. In the system prior to heating to reaction temperature, CO pressures should be from about 500 psi (3.4 MPa) to about 2,700 psi (18.6 MPa), preferably 700 psi (4.8 MPa) to 1800 psi (12.4 MPa). Equivalent concentrations of formic acid, which thermally decomposes into CO and water, may be used for convenience. Inorganic hydroxide or carbonate base, preferably of Group I and II metals and iron and nickel, more preferably sodium may be added in stoichiometric or excess amounts to form inorganic formate, a preferred hydride ion donor (i.e., a quantitative or stoichiometric amount is based on the amount of CO present). An economical method of carving out the process would also include adding the inorganic hydroxide or carbonate base in stoichiometric or excess concentration to the formic acid. It is also envisioned that other water soluble stable hydride donor reducing agents, e.g. sodium borohydride, or even hydrogen be used in the present invention. Although the process effects the cleavage of bonds it may be used to effect the decrease in content and/or removal of both aromatic N and S. It is typically more effective in S removal in the presence of base. It is, therefore, desirable to add an inorganic base as described previously to the aqueous CO and resource mixture to enhance removal of S. In mixed N and S-containing feeds the choice to add optional inorganic base depends largely on the nature of the feed and process economics. Thus, as compared to processes known in the art, the process of the present invention may be used to provide enhanced conversion of aryl-heteroaryl and biheteroaryl containing structures at the stated CO pressures (concentrations). Organic base may be used in combination with CO to produce the corresponding formate which results in a lower system pressure, and thus may be the economically more preferred route. In order to minimize undesirable side reactions, the chemical process may be carried out using deoxygenated water. Additionally, with respect to resources, e.g. coals, it is known that oxidized coals give lower liquefaction yields, and for that reason it may be economically less desirable to use oxygenated water. In the process, the H:C ratio can be such that the starting material or reactant is highly aromatic and contains a large number of aryl linkages. Ratios of up to about 1.25, preferably up to about 1.0, or more preferably up to 0.65 are suitable. The desired reactions typically may be obtained in high yields in as soon as about 5 minutes at reaction conditions. When the reaction time is not of a sufficient duration to produce quantitative reaction the products nevertheless include lower molecular weight, aromatic heteroatom depleted products and hydrogenated species. Unreacted and/or partially reacted materials can be reacted for longer times or recycled to the conversion process. As used herein conversion means effective cleavage and/or hydrogenation of moieties accompanied by removal (ultimately as ammonia and hydrogen sulfide) of at least a portion of the aromatic heteroatoms, and includes hydrogenation that enhances the ability to remove heteroatoms under process conditions. It is generally evidenced by the formation of lower molecular weight liquid products and gases, typically aromatic hydrocarbons wherein heteroatoms are decreased or absent and wherein heteroaryl moieties are dearomatized. These liquid products are generally higher value added materials due to their suitability for use in other applications.

When the starting material is a low H:C ratio resource material such as coal, the material should be crushed or otherwise reduced in particle size. Coals preferably in pieces of less than about 1.27 cm, more preferably less than about 0.64 cm or smaller may be used. For solid materials smaller particle sizes, e.g. 200 Tyler mesh are more desirable. Water to starting material ratios of from about 10:1 to 0.5:1 preferably 5:1 to 1:1, more preferably about 2:1 to 1:1 are highly desirable. The operating parameters of temperature, pressure, residence or reaction time and in a continuous system, flow velocity, may be balanced within the disclosed ranges to achieve the desired products.

C. Procedures

1. General Procedure for Biological Oxidation Reactions

The present invention involves using an organism or enzyme capable of oxidizing aromatic hydrocarbons in order to activate them for further chemical processing.

Some of the strains that are capable of oxidizing aromatic hydrocarbons are presented in Table 1 and Table 2.

In a typical reaction, 100 mg of aromatic compound is added to cells (2 ml of $OD_{600}$=2.0) suspended in 50 mM phosphate buffer (pH=7.25) containing 20 mM glucose. Reaction mixtures are shaken at 250 rpm and incubated at between 5 and 100° C. for up to 5 hours at an air or oxygen partial pressure of between 1 and 10 atm. The reaction mixture is extracted with methylene chloride and gas chromatographic (GC) analysis indicates complete conversion of the starting aromatic compound. High Pressure Liquid Chromatography (HPLC) analysis has been used to identify the oxidized products.

2. General Procedure for Aquathermal Reactions

The thermolyses and aquathermolyses of the hydroxylated compounds were studied in the following systems: (i)

cyclohexane ($C_6H_{12}$); (ii) water ($H_2O$); (iii) 15% aqueous formic acid ($HCO_2H$); and (iv) 15% aqueous sodium formate ($HCO_2Na$). Reactions in cyclohexane (i) allows us to differentiate thermal from aqueous chemistry in (ii). Reactions in 15% $HCO_2H$ (iii) simulate $CO$—$H_2O$ systems with an initial 900 psi cold charge of CO and (iv) simulates $CO$—$H_2O$-base systems.

Water, 15% aqueous formic acid, 15% aqueous sodium formate, and cyclohexane were deoxygenated with argon for 1 hour just before use. All the GC analyses were carried out on a Hewlett Packard 5890 gas chromatograph operated in the split injection mode (30:1 ratio) and equipped with a flame ionization detector (FID). A 30 m capillary column (SPB-5) was used and the oven temperature was programmed from 40 to 250° C. with the initial time set at 1 min. and a subsequent rate of 5° C./min. The flow rate of the helium carrier gas, hydrogen, and air at room temperature (23° C.) were measured at 29, 39, and 380 mL/min. GC/MS analyses of all compounds were performed on a Varian 3400 gas chromatograph and a Finnigan MAT 700 ion trap detector.

All aquathermal experiments were carried out in small (0.75 in.) stainless steel Swagelok (plug and cap) bombs which were not equipped for the collection or analysis of gaseous products. The model compound (0.16 g) and either deoxygenated cyclohexane or an aqueous solvent (1.14 mL) was charged into the nitrogen-blanketed stainless steel bomb which was then sealed. The reactor was then placed, without agitation, in a Techne fluidized sandbath (Model SBS-4) set at 460° C. using a Techne temperature controller (TC-8D) for a time period indicated at a given temperature (2 min heat-up time to 460° C.). After the reaction time period, the reaction was immediately quenched by cooling the bomb sequentially with cold air and dry ice, and the bombs were carefully opened while the contents were still solidified (at −78° C.), to minimize loss of material. The bomb was then resealed and allowed to warm to room temperature before being carefully opened again.

The product mixture was transferred to a glass vial, being careful to recover the maximum amount of reaction mixture from the reaction vessel. The reaction vessel was then rinsed in diethyl ether and this organic fraction was combined with the reaction mixture. After warming to room temperature, the reaction mixture was extracted with diethyl ether (2×3 mL) and the ether layers combined in a separate glass vial.

An initial GC analysis was performed on the ether solution prior to addition of internal standard. This procedure helps to determine the choice of standard since it is important that the GC peak for the internal standard does not obscure any of the product peaks. An accurately weighed amount of the internal standard, heptane (ca. 0.050 g), was then added to the ether solution and the resultant solution was again subjected to GC analysis. From the GC traces obtained the reaction mixture was analyzed in a quantitative fashion and the mass of a particular product could be obtained and its yield determined.

TABLE 1

Strains utilized for oxidation of aromatic compounds are listed below:
Monocyclic dioxygenase class of catabolic pathway

| Strain or plasmid | Compound Accumulated | Partial list of substrates oxidized |
|---|---|---|
| *Pseudomonas putida* F39/D Mutant of strain F1 blocked in the dehydrogenase step | cis-dihydrodiol | Benzene, toluene, ethylbenzene, other monocyclics Naphthalene and biphenyl |

TABLE 1-continued

Strains utilized for oxidation of aromatic compounds are listed below:
Monocyclic dioxygenase class of catabolic pathway

| Strain or plasmid | Compound Accumulated | Partial list of substrates oxidized |
|---|---|---|
| *Pseudomonas putida* F107 Mutant of strain F1 blocked in the catechol dioygenase step | 1,2-dihydroxy | Benzene, toluene, ethylbenzene, other monocyclics Naphthalene and biphenyl |
| pDTG601 Clone containing the aromatic dioxygenase genes from *Pseudomonas putida* F1 | cis-dihydrodiol | Benzene, toluene, ethylbenzene, other monocyclics Naphthalene and biphenyl |
| pDTG602 Clone containing the aromatic dioxygenase and dehydrogenase genes from *Pseudomonas putida* F1 | 1,2-dihydroxy | Benzene, toluene, ethylbenzene, other monocyclics Naphthalene and biphenyl |
| pGJZ1151* Clone containing the aromatic dioxygenase genes from strain GZ9 | cis-dihydrodiol | Benzene, toluene, ethylbenzene, other monocyclics Naphthalene and biphenyl |
| pGJZ1110* Clone containing the aromatic dioxygenase and dehydrogenase genes from strain GZ9 | 1,2-dihydroxy | Benzene, toluene, ethylbenzene, other monocyclics Naphthalene and biphenyl |

TABLE 2

Additional strains utilized for oxidation of aromatic compounds are listed below
Polycyclic dioxygenase class of catabolic pathway

| Strain or plasmid | Compound Accumulated | Partial list of substrates oxidized |
|---|---|---|
| pGJZ1403 Clone containing the aromatic dioxygenase genes from Pseudomonas sp. strain XPW-2 | cis-dihydrodiol | Naphthalene, anthracene, phenanthrene, biphenyl, pyrene, 3-phenoxytoluene, diphenylmethane, dibenzothiophene |
| pGJZ1751* Clone containing the aromatic dioxygenase genes from *Comamonas testosteroni* GZ39 | cis-dihydrodiol | Naphthalene, phenanthrene |
| pGJZ1752* Clone containing the aromatic dioxygenase and dehydrogenase genes from *Comamonas testosteroni* GZ39 | 1,2-dihydroxy | Naphthalene, phenanthrene |
| *Sphingomonas yanoikuyae* B8/36 (formerly known as Beijerinckia sp. strain B8/36) Mutant of strain B1 blocked in the dehydrogenase step | cis-dihydrodiol | Biphenyl, naphthalene, phenanthrene, anthracene, benzo(a)pyrene, benz(a)anthracene, diphenylmethane, dibenzothiophene, carbazole, acenaphthene, acenaphthylene, dibenzo-p-dioxin |
| *Sphingomonas yanoikuyae* EK3* blocked in the dehydrogenase step | cis-dihydrodiol | Same as above for B8/36 |
| *Sphingomonas yanoikuyae* EK16* blocked in the catechol dioxygenase step | 1,2-dihydroxy | Same as above for B8/36 |

EXAMPLE 1 a) Table 3 illustrates that biphenyl which has been oxidized by an organism as listed in Examples 1 and 2 to produce a dihydroxybiphenyl can now be reacted to effect cleavage and hydrogenation.

b) Table 3 illustrates that biphenyl, when activated by hydroxylation is more reactive under aqueous-CO reaction conditions to cleavage and hydrogenation reactions. The formation of phenols, alkylphenols and alkylbenzenes represent cleavage products. The formation of cyclopentyl- and cyclohexylbenzenes and of dihydronaphthalenes represent hydrogenated products which because of the weaker aromatic C-to-aliphatic C bond are more reactive to further bond cleavage reactions. It should be noted that the aromatic C—C bond in biphenyl is quite difficult to cleave. After 1 hour at 460° C. in cyclohexane, water, 15% formic acid and 15% sodium formate no reaction of biphenyl was observed.

TABLE 3

| T (° C.) | t (hr) | Medium | % Conv. | Major Products |
|---|---|---|---|---|
| 4,4'-Dihydroxybiphenyl | | | | |
| 460 | 1 | Cyclohexane | 5.9 | Reactions with solvent medium |
| 460 | 1 | Water | 0.4 | — |
| 460 | 1 | 15% Formic Acid | 1.9 | — |
| 460 | 1 | 15% Sodium Formate | 100 | Phenol (22.4%), Alkylphenols (24.9%), Monohydroxybiphenyls (2.7%) |
| 400 | 2 | 30% Sodium Formate | 57.4 | Phenol (11.1%), Alkylphenols (7.5%), Methylated dihydroxybiphenyls (35.3%) |
| 3,4-Dihydroxybiphenyl | | | | |
| 315 | 2 | Cyclohexane | 0 | |
| 315 | 2 | Water | 0 | |
| 315 | 2 | 15% Formic Acid | 2.9 | |
| 315 | 2 | 15% Sodium Formate | 15.9 | Phenol (22.4%), Alkylphenols (24.9%), Monohydroxybiphenyls (2.7%) |
| 315 | 2 | 15% Sodium Formate | 99.8 | Alkylbenzenes (0.4%), Cyclohexyl-and cyclopentylbenzenes (49%), Monohydroxybiphenyls (15%) |
| 400 | 2 | Cyclohexane | 13.8 | Cyclopentylbenzenes (0.8%), Monohydroxybiphenyls (12.9%) |
| 400 | 2 | Water | 2.3 | Cyclopentylbenzenes (0.3%), Monohydroxybiphenyls (2.0%) |
| 400 | 2 | 15% Formic Acid | 16.4 | Cyclopentylbenzenes (1.8%), Monohydroxybiphenyls (14.7%) |
| 400 | 0.5 | 15% Sodium Formate | 100 | Alkylbenzenes (4%), Cyclohexyl-and cyclopentylbenzenes (58%), Monohydroxybiphenyls (15%), Dihydronaphthalenes (3%) |

TABLE 3-continued

| T (° C.) | t (hr) | Medium | % Conv. | Major Products |
|---|---|---|---|---|
| 3,4-Dihydroxybiphenyl | | | | |
| 460 | 0.12 | Cyclohexane | 11.8 | Cyclopentylbenzenes (0.7%), Monohydroxybiphenyls (11.1%) |
| 460 | 0.12 | Water | 1.0 | Monohydroxybiphenyls (1.0%) |
| 460 | 0.12 | 15% Formic Acid | 5.5 | Cyclopentylbenzenes (0.6%), Monohydroxybiphenyls (4.9%) |
| 460 | 0.12 | 15% Sodium Formate | 100 | Alkylbenzenes (9%), Cyclopentyl-and cyclohexylbenzenes (49%), Monohydroxybiphenyls (15%), Dihydronaptlthalenes (5%) |
| 2,3-Dihydroxybiphenyl | | | | |
| 315 | 6 | 15% Sodium Formate | 82 | Alkylbenzenes (1.3%), Cyclopentyl-and cyclohexylbenzenes (56%), Monohydroxybiphenyls (12%) |
| 400 | 0.25 | 15% Sodium Formate | 91 | Alkylbenzenes (3%), Cyclopentyl-and cyclohexylbenzenes (44%), Monohydroxybiphenyls (14%) |
| 460 | 0.12 | 15% Sodium Formate | 100 | Alkylbenzenes (10%), Cyclopentyl-and cyclohexylbenzenes (56%), Monohydroxybiphenyls (7.5%) |

EXAMPLE 2

Following the procedure of Example 1 the reactivity of a series of phenylquinolines was studied. The phenyl-to-quinoline ring bond is a type of biphenyl (or more accurately biaryl) bond which is difficult to react. Table 4 illustrates that 2-phenylquinoline shows low conversion reactivity in water, 15% formic acid and 15% sodium formate. This is clearer in the right side of the table wherein the % conversion to denitrogenated products-which requires at least partial hydrogenation of the quinoline ring, and the percent cleavage of the aromatic C—C biphenyl bond is illustrated. However, when hydroxyl groups are placed on the 4-position and on both the 3- and 4-positions of the quinoline rings total conversion becomes quantitative and the percent denitrogenation and cleavage of the biaryl linkage are dramatically increased.

TABLE 4

EFFECT OF HYDROXYL GROUPS ON DENITROGENATION AND BIARYL BOND CLEAVAGE UNDER SUPERCRITICAL AQUEOUS CONDITIONS

| | 460° C., 1 Hour | | | | | |
|---|---|---|---|---|---|---|
| | % Conversion | | | % Conversion to Denitrogenated Products (Total % Biaryl Cleavage) | | |
| | $H_2O$ | 15% HCOOH | 15% HCOONa | $H_2O$ | 15% HCOOH | 15% HCCONa |
| 2-Phenylquinoline | 0 | 61 | 16 | — | 10(28) | 2(5) |
| 2-Phenyl-4-hydroxyquinoline | 100 | 100 | 100 | 44(47) | 63(91) | 55(>80) |
| 2-Phenyl-3,4-dihydroxyquinoline | 100 | 100 | 100 | 43(87) | 46(88) | 39(67) |

What is claimed is:

1. A process for transforming aromatic organic compounds and/or resource materials containing aromatic organic compounds comprising:
   (a) contacting a material having at least one aromatic or heterocyclic aromatic ring with a microorganism or biocatalyst in an aqueous medium in order to add a hydroxyl group to said aromatic ring or said heterocyclic aromatic ring of said material, and
   (b) transforming in an aqueous medium said material whose aromatic ring or heterocyclic aromatic ring includes a hydroxyl group so as to cause hydrogenation and/or hydrogenolysis of said aromatic ring or heteroycyclic ring of said material.

2. The process of claim 1 wherein said microorganisms or biocatalysts are capable of oxidizing aromatic materials and are selected from a group comprising, but not limited to, bacteria, fungi, or fractions and/or combinations thereof.

3. The process of claim 1(a) wherein said contacting is performed by contacting the feed with an aqueous or essentially non-aqueous mixture containing an organism or biocatalyst capable of hydroxylating aromatic compounds at a temperature between 5° C. and 100° C. and at an air or oxygen pressure of between 1 and 10 atm.

4. The process of claim 1(b) wherein said transforming step to cause hydrogenation and/or hydrogenolysis is performed by contact with water in the absence of externally supplied hydrogen in the presence of an agent selected from the group consisting of carbon monoxide and optional base and optional water stable hydride donors, controlling the temperature in a range from above about 200° C. to 600° C. and continuing said transforming step for a time sufficient to effect said conversion and upgrading to produce lower molecular weight hydrogen enriched and lower heteroatom containing products.

5. The process of claim 4 wherein said temperature is between 250 and 550° C.

6. The process of claim 4 wherein said temperature is between 300 and 500° C.

7. The process of claim 4 wherein said pressure is between 500 and 2700 psi.

8. The process of claim 4 wherein said pressure is between 700 and 1800 psi.

9. The process of claim 4 wherein carbon monoxide is reacted to form a species capable of transferring hydride ions to said aromatic ring.

10. The process of claim 4 wherein carbon monoxide is generated by decomposition of formic acid.

11. The process of claim further comprising adding an inorganic hydroxide or carbonate base, selected from the group consisting of Group I and II metals, iron and nickel.

12. The process of claim 4 wherein said water stable inorganic hydride donor selected from the group of metal formates, metal borohydrides, metal hydrides.

13. The process of claim 1(b) wherein the water is substantially free of dissolved oxygen.

14. The process of claim 1(b) wherein the weight ratio of water to organic resource material is about 0.5 to about 10.0.

15. The process of claim 1 wherein the weight ratio (water/feed) is about 0.5 to about 5.0.

16. The process of claim 2 wherein the organic resource material has a maximum particle diameter ranging from about 0.25 inches to 200 Tyler mesh.

17. The process of claim 1 wherein the maximum particle diameter ranges from about 60 to about 100 Tyler mesh.

18. The process of claim 1(b) wherein said amount of agent is equivalent to a concentration level in water in the range from about 0.01 to about 15 weight percent.

19. The process of claim 4 wherein said effective amount of agent is equivalent to a concentration level in water in the range of about 0.1 to about 10 weight percent.

20. The process of claim 1 further comprising recontacting the products obtained in claim 1 with the organic resource material and thereby effect further conversion and upgrading.

21. The process of claim 1(b) wherein neutral water is charged into the reactor.

* * * * *